(12) United States Patent
Fanger et al.

(10) Patent No.: US 8,394,107 B2
(45) Date of Patent: *Mar. 12, 2013

(54) GUIDE FOR SPINAL TOOLS, IMPLANTS, AND DEVICES

(75) Inventors: Jonathan Fanger, Raynham, MA (US); Eric D. Kolb, Sandy Hook, CT (US); Glen Arthur Presbrey, Pascoag, RI (US)

(73) Assignee: DePuy Spine, Inc., Raynham, MA (US)

( * ) Notice: Subject to any disclaimer, the term of this patent is extended or adjusted under 35 U.S.C. 154(b) by 105 days.

This patent is subject to a terminal disclaimer.

(21) Appl. No.: 12/838,013

(22) Filed: Jul. 16, 2010

(65) Prior Publication Data

US 2011/0015685 A1 Jan. 20, 2011

Related U.S. Application Data

(63) Continuation of application No. 10/776,414, filed on Feb. 11, 2004, now Pat. No. 7,776,047, which is a continuation-in-part of application No. 10/664,575, filed on Sep. 17, 2003, now Pat. No. 7,935,123, which is a continuation-in-part of application No.

(Continued)

(51) Int. Cl.
  *A61B 17/58* (2006.01)
  *A61B 17/60* (2006.01)
  *A61F 2/00* (2006.01)

(52) U.S. Cl. .......................................... 606/96

(58) Field of Classification Search .............. 606/96–99, 606/86 R, 84, 79, 86 A, 281, 53, 59, 60, 246, 606/279, 62, 280, 80, 87, 247, 249, 250; 623/17.11–17.16

See application file for complete search history.

(56) References Cited

U.S. PATENT DOCUMENTS

| 1,920,821 | A | 8/1933 | Wassernaar |
| 2,466,023 | A | 4/1949 | Griffin |
| 2,486,303 | A | 10/1949 | Longfellow |
| 2,494,229 | A | 1/1950 | Wollpert et al. |

(Continued)

FOREIGN PATENT DOCUMENTS

| DE | 4201043 | 1/1992 |
| EP | 0897697 A1 | 2/1999 |

(Continued)

OTHER PUBLICATIONS

Product Literature, by SYNTHES Spine, The Cervical Spine Locking Plate CSLP, 2000.

(Continued)

*Primary Examiner* — Alvin J. Stewart
(74) *Attorney, Agent, or Firm* — Nutter McClennen & Fish LLP

(57) ABSTRACT

A guide device is provided for use with a spinal fixation element that has at least one pair of thru bores formed therein. The guide device generally includes an elongate shaft having a proximal end and a distal end. A guide member is coupled to the distal end of the elongate shaft and it includes at least one pathway extending therethrough, and at least one alignment element that is positioned distal of the guide member. Each alignment element(s) is adapted to interact with a spinal fixation element to position the guide member with respect to the spinal fixation element such that the each pathway in the guide member is aligned with a corresponding thru bore formed in the spinal fixation element. The guide member can then be used to guide tools, devices, and/or implants through each pathway in the spinal fixation element and into bone.

18 Claims, 11 Drawing Sheets

Related U.S. Application Data

10/409,958, filed on Apr. 9, 2003, now Pat. No. 7,416,553, application No. 12/838,013, which is a continuation-in-part of application No. 10/609,123, filed on Jun. 27, 2003, now Pat. No. 7,909,829.

(56) References Cited

U.S. PATENT DOCUMENTS

| | | |
|---|---|---|
| 2,695,688 A | 11/1954 | Wollpert et al. |
| 2,756,742 A | 7/1956 | Barton |
| 3,244,170 A | 4/1966 | McElvenny |
| 3,463,148 A | 8/1969 | Allgower et al. |
| 3,552,389 A | 1/1971 | Allgower et al. |
| 3,596,656 A | 8/1971 | Kaute et al. |
| 3,626,471 A | 12/1971 | Florin |
| 3,659,595 A | 5/1972 | Haboush |
| 3,695,259 A | 10/1972 | Yost |
| 3,716,050 A | 2/1973 | Johnston |
| 3,779,240 A | 12/1973 | Kondo et al. |
| 3,824,995 A | 7/1974 | Getscher et al. |
| 3,900,025 A | 8/1975 | Barnes, Jr. |
| RE28,841 E | 6/1976 | Allgower et al. |
| 4,119,092 A | 10/1978 | Gil et al. |
| 4,187,841 A | 2/1980 | Knutson |
| 4,219,015 A | 8/1980 | Steinemann et al. |
| 4,224,699 A | 9/1980 | Weber et al. |
| 4,257,411 A | 3/1981 | Cho |
| 4,388,921 A | 6/1983 | Sutter et al. |
| 4,408,601 A | 10/1983 | Wenk et al. |
| 4,454,876 A | 6/1984 | Mears |
| RE31,628 E | 7/1984 | Allgower et al. |
| 4,493,317 A | 1/1985 | Klaue et al. |
| 4,502,475 A | 3/1985 | Weigle et al. |
| 4,503,848 A | 3/1985 | Caspar et al. |
| 4,513,744 A | 4/1985 | Klaue et al. |
| 4,524,765 A | 6/1985 | de Zbikowski |
| 4,541,424 A | 9/1985 | Grosse et al. |
| 4,651,724 A | 3/1987 | Berentey et al. |
| 4,686,972 A | 8/1987 | Kurland |
| 4,733,657 A | 3/1988 | Kluger |
| 4,744,353 A | 5/1988 | McFarland |
| 4,773,402 A | 9/1988 | Asher et al. |
| 4,800,874 A | 1/1989 | David et al. |
| 4,838,252 A | 6/1989 | Klaue et al. |
| 4,848,327 A | 7/1989 | Perdue |
| 4,887,596 A | 12/1989 | Sherman |
| 4,936,844 A | 6/1990 | Chandler et al. |
| 4,957,495 A | 9/1990 | Kluger |
| 5,002,544 A | 3/1991 | Klaue et al. |
| 5,006,120 A | 4/1991 | Carter |
| 5,041,113 A | 8/1991 | Biedermann et al. |
| 5,041,114 A | 8/1991 | Chapman et al. |
| 5,041,133 A | 8/1991 | Sayano et al. |
| 5,052,373 A | 10/1991 | Michelson |
| 5,053,036 A | 10/1991 | Perren et al. |
| 5,059,194 A | 10/1991 | Michelson |
| 5,067,477 A | 11/1991 | Santangelo |
| 5,088,472 A | 2/1992 | Fakhrai |
| 5,129,899 A | 7/1992 | Small et al. |
| 5,129,903 A | 7/1992 | Luhr et al. |
| 5,147,361 A | 9/1992 | Ojima et al. |
| 5,151,103 A | 9/1992 | Tepic et al. |
| 5,180,381 A | 1/1993 | Aust et al. |
| 5,234,290 A | 8/1993 | Collins |
| 5,275,601 A | 1/1994 | Gogolewski et al. |
| 5,303,694 A | 4/1994 | Mikhail |
| 5,306,278 A | 4/1994 | Dahl et al. |
| 5,318,567 A | 6/1994 | Vichard et al. |
| 5,324,290 A | 6/1994 | Zdeblick et al. |
| 5,324,295 A | 6/1994 | Shapiro |
| 5,336,224 A | 8/1994 | Selman |
| 5,342,295 A | 8/1994 | Imran |
| 5,364,399 A | 11/1994 | Lowery et al. |
| 5,365,921 A | 11/1994 | Bookwalter et al. |
| 5,415,660 A | 5/1995 | Campbell et al. |
| 5,423,826 A | 6/1995 | Coates et al. |
| 5,439,463 A | 8/1995 | Lin |
| 5,501,684 A | 3/1996 | Schlapfer et al. |
| 5,520,690 A | 5/1996 | Errico et al. |
| 5,531,746 A | 7/1996 | Errico et al. |
| 5,531,751 A | 7/1996 | Schultheiss et al. |
| 5,534,027 A | 7/1996 | Hodorek |
| 5,549,612 A | 8/1996 | Yapp et al. |
| 5,558,622 A | 9/1996 | Greenberg |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,607,428 A | 3/1997 | Lin |
| 5,616,142 A | 4/1997 | Yuan et al. |
| 5,616,144 A | 4/1997 | Yapp et al. |
| 5,643,265 A | 7/1997 | Errico et al. |
| 5,651,283 A | 7/1997 | Runciman et al. |
| 5,669,915 A | 9/1997 | Caspar et al. |
| 5,672,177 A | 9/1997 | Seldin |
| 5,676,666 A | 10/1997 | Oxland |
| 5,713,904 A | 2/1998 | Errico et al. |
| 5,735,853 A | 4/1998 | Olerud |
| 5,745,884 A | 4/1998 | Carnegie et al. |
| 5,749,873 A | 5/1998 | Fairley et al. |
| 5,749,884 A | 5/1998 | Benderev et al. |
| 5,755,721 A | 5/1998 | Hearn |
| 5,788,630 A | 8/1998 | Furnish |
| 5,807,396 A | 9/1998 | Raveh |
| 5,827,286 A | 10/1998 | Incavo et al. |
| 5,836,950 A | 11/1998 | Hansson |
| RE36,020 E | 12/1998 | Moore et al. |
| 5,846,193 A | 12/1998 | Wright |
| 5,851,207 A | 12/1998 | Cesarone |
| 5,865,848 A | 2/1999 | Baker |
| 5,876,402 A | 3/1999 | Errico et al. |
| 5,885,286 A | 3/1999 | Sherman et al. |
| 5,888,204 A | 3/1999 | Ralph et al. |
| 5,904,683 A | 5/1999 | Pohndorf et al. |
| 5,931,838 A | 8/1999 | Vito |
| 5,951,558 A | 9/1999 | Fiz |
| 5,954,722 A | 9/1999 | Bono |
| 5,964,762 A | 10/1999 | Biedermann et al. |
| 5,964,763 A | 10/1999 | Incavo et al. |
| 5,967,141 A | 10/1999 | Heinonen et al. |
| 5,967,171 A | 10/1999 | Dwyer, Jr. |
| 5,984,926 A | 11/1999 | Jones |
| 6,006,581 A | 12/1999 | Holmes |
| 6,017,345 A | 1/2000 | Richelsoph |
| 6,030,389 A | 2/2000 | Wagner et al. |
| 6,039,740 A | 3/2000 | Olerud et al. |
| 6,063,090 A | 5/2000 | Schlapfer et al. |
| 6,066,142 A | 5/2000 | Serbousek et al. |
| 6,066,175 A | 5/2000 | Henderson et al. |
| 6,106,527 A | 8/2000 | Wu et al. |
| 6,113,602 A | 9/2000 | Sand |
| 6,117,173 A | 9/2000 | Taddia et al. |
| 6,132,432 A | 10/2000 | Richelsoph |
| 6,139,550 A | 10/2000 | Michelson |
| D433,506 S | 11/2000 | Asfora |
| 6,143,012 A | 11/2000 | Gausepohl et al. |
| 6,152,927 A | 11/2000 | Farris et al. |
| 6,159,244 A | 12/2000 | Suddaby |
| 6,193,721 B1 | 2/2001 | Michelson |
| 6,200,348 B1 | 3/2001 | Biedermann et al. |
| 6,206,828 B1 | 3/2001 | Wright |
| 6,206,881 B1 | 3/2001 | Frigg et al. |
| 6,224,602 B1 | 5/2001 | Hayes |
| 6,227,124 B1 | 5/2001 | Gaydos et al. |
| 6,228,085 B1 | 5/2001 | Theken et al. |
| 6,235,033 B1 | 5/2001 | Brace et al. |
| 6,235,034 B1 | 5/2001 | Bray |
| 6,241,731 B1 | 6/2001 | Fiz et al. |
| 6,258,092 B1 | 7/2001 | Dall et al. |
| 6,258,098 B1 | 7/2001 | Taylor et al. |
| 6,261,291 B1 | 7/2001 | Talaber et al. |
| 6,273,889 B1 | 8/2001 | Richelsoph |
| 6,277,124 B1 | 8/2001 | Haag |
| 6,293,949 B1 | 9/2001 | Justis et al. |
| 6,306,136 B1 | 10/2001 | Baccelli |

| | | |
|---|---|---|
| 6,306,139 B1 | 10/2001 | Fuentes et al. |
| 6,309,393 B1 | 10/2001 | Tepic et al. |
| 6,322,562 B1 | 11/2001 | Wolter et al. |
| 6,328,738 B1 | 12/2001 | Suddaby |
| 6,331,179 B1 | 12/2001 | Freid et al. |
| 6,332,887 B1 | 12/2001 | Knox |
| 6,340,363 B1 | 1/2002 | Bolger et al. |
| 6,342,055 B1 | 1/2002 | Eisermann et al. |
| 6,342,056 B1 | 1/2002 | Mac-Thiong et al. |
| 6,342,057 B1 | 1/2002 | Brace et al. |
| 6,379,364 B1 | 4/2002 | Brace et al. |
| 6,402,756 B1 | 6/2002 | Ralph et al. |
| 6,413,259 B1 | 7/2002 | Lyons et al. |
| 6,416,518 B1 | 7/2002 | DeMayo |
| 6,419,678 B1 | 7/2002 | Asfora |
| 6,428,542 B1 | 8/2002 | Michelson |
| 6,441,602 B1 | 8/2002 | Eckhardt et al. |
| 6,447,512 B1 | 9/2002 | Landry et al. |
| 6,454,769 B2 | 9/2002 | Wagner et al. |
| 6,503,250 B2 | 1/2003 | Paul |
| 6,511,484 B2 | 1/2003 | Torode et al. |
| 6,524,318 B1 | 2/2003 | Longhini et al. |
| 6,527,776 B1 | 3/2003 | Michelson |
| 6,533,786 B1 | 3/2003 | Needham et al. |
| 6,545,769 B2 | 4/2003 | Collard et al. |
| 6,565,571 B1 | 5/2003 | Jackowski et al. |
| 6,575,975 B2 | 6/2003 | Brace et al. |
| 6,585,738 B1 | 7/2003 | Mangione et al. |
| 6,592,586 B1 | 7/2003 | Michelson |
| 6,595,993 B2 | 7/2003 | Donno et al. |
| 6,602,255 B1 | 8/2003 | Campbell et al. |
| 6,602,257 B1 | 8/2003 | Thramann |
| 6,620,163 B1 | 9/2003 | Michelson |
| 6,641,613 B2 | 11/2003 | Sennett |
| 6,652,525 B1 | 11/2003 | Assaker et al. |
| 6,656,181 B2 | 12/2003 | Dixon et al. |
| 6,663,562 B2 | 12/2003 | Chang |
| 6,669,700 B1 | 12/2003 | Farris et al. |
| 6,673,115 B2 | 1/2004 | Resch et al. |
| 6,679,883 B2 | 1/2004 | Hawkes et al. |
| 6,692,503 B2 | 2/2004 | Foley et al. |
| 6,695,846 B2 | 2/2004 | Richelsoph et al. |
| 6,712,818 B1 | 3/2004 | Michelson |
| 6,755,833 B1 | 6/2004 | Paul et al. |
| 6,770,096 B2 | 8/2004 | Bolger et al. |
| 6,793,658 B2 | 9/2004 | LeHuec et al. |
| 6,796,986 B2 | 9/2004 | Duffner |
| 6,913,463 B2 | 7/2005 | Blacklock |
| 6,960,216 B2 | 11/2005 | Kolb et al. |
| 7,011,665 B2 | 3/2006 | Null et al. |
| 7,094,242 B2 | 8/2006 | Ralph et al. |
| 7,147,599 B2 | 12/2006 | Phillips et al. |
| 7,278,997 B1 | 10/2007 | Mueller et al. |
| 7,357,804 B2 | 4/2008 | Binder, Jr. et al. |
| 7,416,553 B2 | 8/2008 | Patel et al. |
| 7,488,327 B2 | 2/2009 | Rathbun et al. |
| 7,776,047 B2 | 8/2010 | Fanger et al. |
| 2001/0009971 A1 | 7/2001 | Sherts et al. |
| 2001/0021851 A1 | 9/2001 | Eberlein et al. |
| 2001/0037112 A1 | 11/2001 | Brace et al. |
| 2001/0047172 A1 | 11/2001 | Foley et al. |
| 2002/0022843 A1 | 2/2002 | Michelson |
| 2002/0022847 A1 | 2/2002 | Ray et al. |
| 2002/0045897 A1 | 4/2002 | Dixon et al. |
| 2002/0045898 A1 | 4/2002 | Freid et al. |
| 2002/0049444 A1 | 4/2002 | Knox |
| 2002/0055741 A1 | 5/2002 | Schlapfer et al. |
| 2002/0058939 A1 | 5/2002 | Wagner et al. |
| 2002/0058940 A1 | 5/2002 | Frigg et al. |
| 2002/0082606 A1 | 6/2002 | Suddaby |
| 2002/0143336 A1 | 10/2002 | Hearn |
| 2002/0147450 A1 | 10/2002 | LeHuec et al. |
| 2002/0151899 A1 | 10/2002 | Bailey et al. |
| 2002/0156474 A1 | 10/2002 | Wack et al. |
| 2002/0183754 A1 | 12/2002 | Michelson |
| 2002/0183757 A1 | 12/2002 | Michelson |
| 2002/0188296 A1 | 12/2002 | Michelson |
| 2002/0198533 A1 | 12/2002 | Geisler et al. |
| 2003/0023242 A1 | 1/2003 | Harrington |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0065251 A1 | 4/2003 | Feng et al. |
| 2003/0083658 A1 | 5/2003 | Hawkes et al. |
| 2003/0135213 A1 | 7/2003 | LeHuec et al. |
| 2003/0181912 A1 | 9/2003 | Michelson |
| 2003/0187436 A1 | 10/2003 | Bolger et al. |
| 2003/0187440 A1 | 10/2003 | Richelsoph et al. |
| 2003/0187442 A1 | 10/2003 | Richelsoph et al. |
| 2003/0187454 A1 | 10/2003 | Gill et al. |
| 2003/0208204 A1 | 11/2003 | Bailey et al. |
| 2003/0229348 A1 | 12/2003 | Sevrain |
| 2003/0233098 A1 | 12/2003 | Markworth |
| 2004/0015169 A1 | 1/2004 | Gause |
| 2004/0015174 A1 | 1/2004 | Null et al. |
| 2004/0019353 A1 | 1/2004 | Freid et al. |
| 2004/0034352 A1 | 2/2004 | Needham et al. |
| 2004/0034354 A1 | 2/2004 | Paul |
| 2004/0087951 A1 | 5/2004 | Khalili |
| 2004/0092947 A1 | 5/2004 | Foley |
| 2004/0097935 A1 | 5/2004 | Richelsoph et al. |
| 2004/0133205 A1 | 7/2004 | Thramann et al. |
| 2004/0204710 A1 | 10/2004 | Patel et al. |
| 2004/0204712 A1 | 10/2004 | Kolb et al. |
| 2004/0204716 A1 | 10/2004 | Fanger et al. |
| 2004/0204717 A1 | 10/2004 | Fanger et al. |
| 2004/0210232 A1 | 10/2004 | Patel et al. |
| 2004/0267274 A1 | 12/2004 | Patel et al. |
| 2005/0021040 A1 | 1/2005 | Bertagnoli |
| 2007/0244489 A1 | 10/2007 | Patel et al. |

FOREIGN PATENT DOCUMENTS

| | | |
|---|---|---|
| FR | 2827150 A1 | 1/2003 |
| WO | WO-9632071 | 10/1996 |
| WO | WO-0022999 | 4/2000 |
| WO | 00/24343 A1 | 5/2000 |
| WO | WO-0064359 | 11/2000 |
| WO | WO-02085226 | 10/2002 |
| WO | WO-03/007826 | 1/2003 |
| WO | WO-03/024344 | 3/2003 |
| WO | WO-03063714 | 8/2003 |

OTHER PUBLICATIONS

Cervi-Lok™ Surgical Technique Manual (pp. 1-19), 1995 SPINETECH Inc.®, L1015 Revision B.

European Search Report for Application No. 04779901.0 issued Jun. 12, 2008. (3 pages).

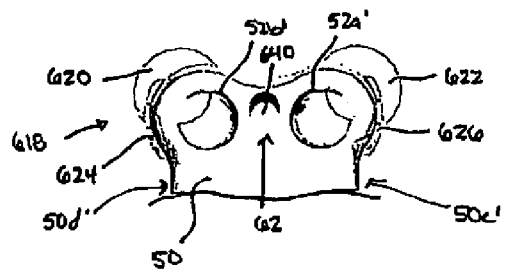
Fig. 6A
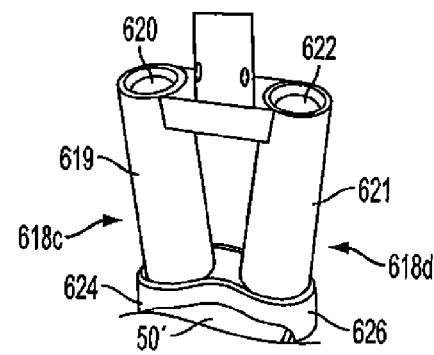
FIG. 6B
Fig. 7
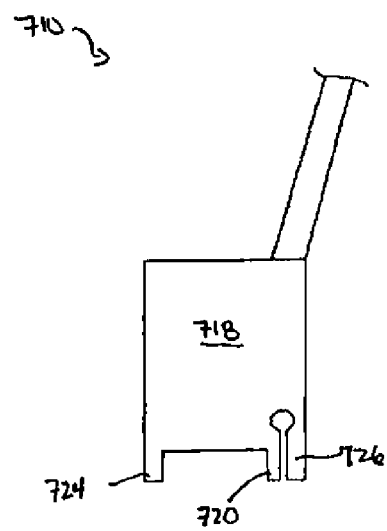

GUIDE FOR SPINAL TOOLS, IMPLANTS, AND DEVICES

CROSS-REFERENCE TO RELATED APPLICATIONS

This application is a continuation of U.S. patent application Ser. No. 10/776,414 filed on Feb. 11, 2004 and entitled "GUIDE FOR SPINAL TOOLS, IMPLANTS AND DEVICES," which is a continuation-in-part of U.S. patent application Ser. No. 10/664,575 filed on Sep. 17, 2003 and entitled "DRILL GUIDE WITH ALIGNMENT FEATURE," which is a continuation-in-part of both U.S. patent application Ser. No. 10/409,958 filed on Apr. 9, 2003 and entitled "DRILL GUIDE AND PLATE INSERTER" and U.S. patent application Ser. No. 10/609,123 filed on Jun. 27, 2003 and entitled "TISSUE RETRACTOR AND DRILL GUIDE," each of which are expressly incorporated by reference herein.

FIELD OF THE INVENTION

The present invention relates to devices for assisting in spinal surgery, and more particularly to a guide for introducing spinal tools and devices.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate that is positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in a proper position and to bridge a weakened or diseased area, such as when a disc, vertebral body or fragment has been removed.

Such fixation plates have been used to immobilize a variety of bones, including vertebral bodies of the spine. These bone plate systems usually include a rigid spinal fixation plate having a plurality of openings. The openings are either holes or slots for screw placement. The spinal fixation plate is placed against the damaged vertebral bodies and bone screws are used to secure the spinal fixation plate to the spine and optionally to a prosthetic implant or bone graft positioned between the adjacent vertebrae. Implantation of the spinal fixation plate, however, can be difficult. Each spinal fixation plate must be properly aligned with the vertebral bodies, and holes for receiving the bone screws must be drilled into the vertebrae at precise angles. It is often necessary to use the spinal fixation plate as a guide for drilling and tapping the bone in preparation for receiving the bone screws. Such a procedure can be difficult, however, as the surgeon is required to securely and rigidly hold the spinal fixation plate against the vertebrae, obtain proper alignment, drill, tap, and finally set the bone screws.

Accordingly, there remains a need for an improved guide device that can be used to facilitate implantation of a spinal fixation element, such as a spinal fixation plate.

SUMMARY OF THE INVENTION

The present invention provides a guide device for use with a spinal fixation element, such as a spinal fixation plate, that has at least one pair of thru bores formed therein. The guide device generally includes an elongate shaft having a proximal end and a distal end. A guide member is coupled to the distal end of the elongate shaft and it includes at least one pathway extending therethrough, and at least one alignment element that is positioned distal of the guide member. Each alignment element(s) is adapted to interact with a spinal fixation element to align each pathway in the guide member with a corresponding thru bore formed in the spinal fixation element. The guide member can then be used to guide tools, implants, and/or devices through each pathway in the spinal fixation element and into bone.

The alignment element(s) can have a variety of configurations, and in one embodiment each alignment element is a tab that extends distally from the guide member. Each tab is preferably adapted to interact with a spinal fixation element to align the guide member with the spinal fixation element, and more preferably the tabs provide a sliding interference fit with the spinal fixation element. In an exemplary embodiment, the guide member includes first and second opposed alignment tabs that extend from opposed outer edges of the guide member either at a substantial mid-portion of the guide member, or such that the at least one pathway is positioned between the first and second alignment tabs. In an alternative embodiment, opposed first and second tabs can extend distally from the guide member, and they can be movable between an open position, and a closed position wherein the tabs are adapted to engage opposed edges of a spinal fixation element. The device can also optionally or alternatively include at least one protrusion that extends distally from the guide member and that is adapted to be disposed within a corresponding bore formed in the spinal fixation element. In another embodiment, the alignment tab can be adapted to be disposed within a corresponding slot formed in a spinal fixation element, and/or the tab(s) can be adapted to prevent rotation between the guide member and a spinal fixation element when the guide member is coupled to the spinal fixation element.

The guide member of the guide device can also have a variety of configurations, and in one embodiment it can have a substantially rectangular, elongate shape with first and second lumens extending therethrough. The guide member can include opposed transverse sides which preferably have a width that is less than a width of opposed superior and inferior sides. In this configuration, the guide device preferably includes a first alignment tab that extends distally from the superior side of the guide member and a second alignment tab that extends distally from the inferior side of the guide member. The tab(s) can be configured to interact with a graft window formed in a spinal fixation element. Alternatively, the guide member can include first and second alignment tabs that extend distally from opposed transverse sides of the guide member. In another embodiment, the guide member can have a first barrel with a lumen extending therethrough, and a second barrel with a lumen extending therethrough. The first and second barrels can be positioned at an angle with respect to one another. For example, a central axis of the first barrel can be non-parallel to a central axis of the second barrel, such that the central axis of the first barrel and the central axis of the second barrel converge relative to one another.

In yet another embodiment of the present invention, the alignment element(s) can be formed on a support member that is coupled to the distal end of the elongate shaft, and the alignment element(s) can be adapted to removably engage a spinal fixation element. The guide member is preferably slidably movable along the support member such that a position of the guide member with respect to a spinal fixation element engaged by the support member is adjustable. The device can also include an engagement mechanism that is formed on a distal end of the elongate shaft and that is adapted to releasably engage the support member such that the position of the guide member can be temporarily fixed. A trigger mechanism can be formed on the proximal end of the elongate shaft and coupled to the engagement mechanism for moving the engagement mechanism between an engaged position, wherein the guide member is fixed at a desired position, and a released position, wherein the guide member is slidably movable along the support member. In an exemplary embodiment, the support member is arch-shaped and each alignment element(s) is in the form of a substantially concave groove that is formed on an inner surface of the support member.

In other aspects of the present invention, the guide device can include an elongate shaft having proximal and distal ends, and a guide member that is coupled to the distal end of the elongate shaft and that is in the form of a substantially hollow housing having first and second pathways extending therethrough between proximal and distal ends thereof. Each pathway can be at least partially in communication with one another, and in an exemplary embodiment the first and second pathways comprise opposed, substantially semi-cylindrical pathways formed within the hollow housing. At least a portion of each pathway can be defined by a substantially elongate, semi-cylindrical sidewall of the housing. In an exemplary embodiment, a distal end of each semi-cylindrical sidewall extends distally beyond a distal end of the guide member to form opposed tabs that are adapted to seat a spinal fixation element therebetween. Each tab preferably has a substantially concave inner surface that is adapted to match the contour of a substantially concave outer surface formed around a perimeter of a spinal fixation element. In another embodiment, the guide member can include at least one cut-out portion formed in the housing between the first and second pathways, and more preferably it includes opposed first and second cut-out portions that extend in a proximal-distal direction, and that are formed substantially between the first and second pathways. The first cut-out portion preferably extends from the distal end of the housing to the proximal end of the housing, and the second cut-out portion preferably extends from the distal end of the housing and terminates distal to the proximal end of the housing.

The present invention also provides a spinal fixation kit that includes a guide device, and a spinal fixation element having at least one thru bore formed therein for receiving a fastening element that is effective to mate the spinal fixation element to at least one vertebrae. The spinal fixation element can also include at least one graft window formed therein that is adjacent to at least one pair of opposed thru bores formed in the spinal fixation element.

BRIEF DESCRIPTION OF THE DRAWINGS

FIG. 6A is a bottom view of a portion of a spinal fixation plate having another embodiment of a guide device coupled thereto in accordance with the present invention;

FIG. 6B is perspective side view of the guide device and spinal fixation plate of FIG. 6A;

FIG. 7 is a side view illustration of portion of another embodiment of a guide device in accordance with the present invention;

DETAILED DESCRIPTION OF THE INVENTION

The present invention provides a guide device that is useful during spinal surgery to facilitate implantation of a spinal fixation element, such as a spinal fixation plate. In general, the device includes an elongate shaft having a proximal end and a distal end that is coupled to a guide member. The guide member includes at least one pathway extending therethrough for receiving a tool. At least one alignment element is positioned distal of the guide member, and it is adapted to interact with a spinal fixation element to position the at least one pathway in the guide member in alignment with at least one corresponding bore formed in the spinal fixation element, thereby providing a fixed entry angle for tools being inserted therethrough. In use, the guide device can be used to drill, awl, tap, and insert tools, devices, and/or implants, such as bone screws, into the vertebral bodies to attach the spinal fixation element thereto.

The guide device is particularly advantageous in that it provides a more time efficient and simplified surgical procedure, eliminating several unnecessary steps and instruments typically required to implant a spinal fixation element, such as a spinal fixation plate. In particular, in one embodiment, the alignment element(s) does not rigidly attach to the spinal fixation element, thus allowing the guide member to advantageously be quickly and easily positioned and aligned with a spinal fixation element. The guide member can also be advantageously configured to have a relatively small profile, unlike some prior art devices. For example, the guide member can include one or more alignment tabs, at least one of which can interact with a graft window formed in a spinal fixation element. Since a graft window is an internal component of a spinal fixation element, the guide member can be positioned over and aligned with the spinal fixation element without impinging on any adjacent soft tissues that may be located at the lateral edges of the spinal fixation element. In other embodiments, the guide member can include one or more windows formed therein for facilitating visual access of the surgical site and of tools or devices being introduced through the guide member.

Figure 1:
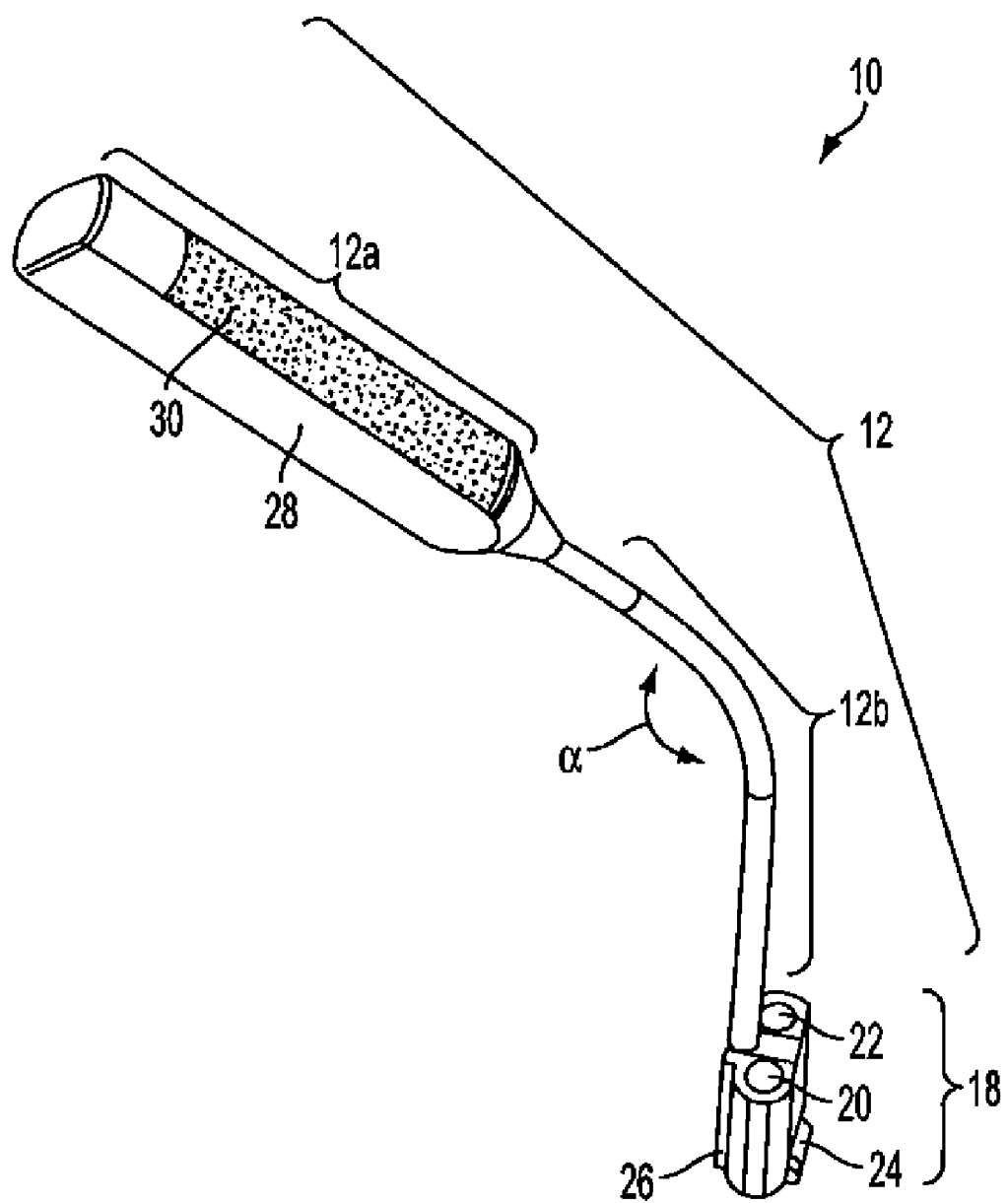
FIG. 1 is a perspective view of one embodiment of a guide device in accordance with the present invention.

FIG. 1 illustrates one embodiment of a guide device 10 in accordance with the present invention. As shown, the device 10 generally includes an elongate shaft 12 having a proximal portion 12a, and a distal portion 12b that is coupled to a guide member 18. The guide member 18 includes first and second pathways in the form of lumens 20, 22 formed therein and extending therethrough. The lumens 20, 22 are adapted to be aligned with corresponding thru bores formed in a spinal fixation element when the guide member 18 is coupled to a spinal fixation element. The guide member can also include features for facilitating alignment of the guide member 18 with a spinal fixation element, as will be discussed in more detail below.

The elongate shaft 12 of device 10 can have a variety of configurations, shapes and sizes, but in an exemplary embodiment, the proximal portion 12a is adapted to extend out of a patient's body, while the distal portion 12b is coupled to the guide member 18, which can be inserted into a surgical incision within in the patient's body. The distal end 12b can optionally be adapted to retract tissue, as is described in related U.S. patent application Ser. No. 10/609,123, which is incorporated herein by reference in its entirety. The proximal and distal portions 12a, 12b can be fixedly attached to, removably mated to, or integrally formed with one another, but preferably a portion of the shaft 12 is disposed at an angle α such that the proximal portion 12a is offset from the guide member 18 to facilitate visual and physical access to the surgical site. While the angle α in the shaft 12 can vary, in an exemplary embodiment, the angle α is in the range of about 110° to 160°, and more preferably it is in the range of about 125° to 145°. While only a single angle is shown, a person skilled in the art will appreciate that the elongate member 12 can include two or more bends to facilitate visual access to the surgical site and/or to facilitate positioning of the device 10 in the patient's body. Moreover, the proximal portion 12a can optionally be adjustably movable with respect to the distal portion 12b to allow the surgeon to adjust the angle and/or position of the proximal portion 12a with respect to the distal portion 12b.

The proximal portion 12a of elongate member 12 can have a variety of configurations, but it preferably includes a handle 28 formed thereon or mated thereto. The handle 28 can have virtually any shape and size, and it can optionally include a gripping surface 30, such as a knurled surface, ridges, or grooves, to further facilitate grasping of the device 10. In an alternative embodiment, or in addition to the handle 28, the proximal portion 12a of the elongate member 12 can include a clamp member (not shown) formed thereon or mated thereto that is effective to mate the device 10 to a surgical retractor, such as, for example a Bookwalter retractor. Alternatively, the surgical retractor can contain a post or surface for attaching to a Bookwalter retractor having a clamp. A person skilled in the art will appreciate that a variety of clamp members and/or other mating techniques can be used to mate the device 10 to a retractor or other type of support member.

The distal portion 12b of the elongate member 12 can also have a variety of shapes and sizes, but it should be adapted to couple to the guide member 18. In an exemplary embodiment, the distal portion 12b is fixedly attached to or integrally formed with the guide member 18 at a location that is substantially between, but offset from the center axis of the first and second lumens 20, 22 in the guide member 18. This offset design will provide better visual and physical access to the guide member 18, since the elongate shaft 12 extends from a side of the guide member 18. A person skilled in the art will appreciate that the distal portion 12b of the elongate member 12 can be removably mated to the guide member 18, and/or it can be mated to virtually any portion of the guide member 18.

Figure 2A:
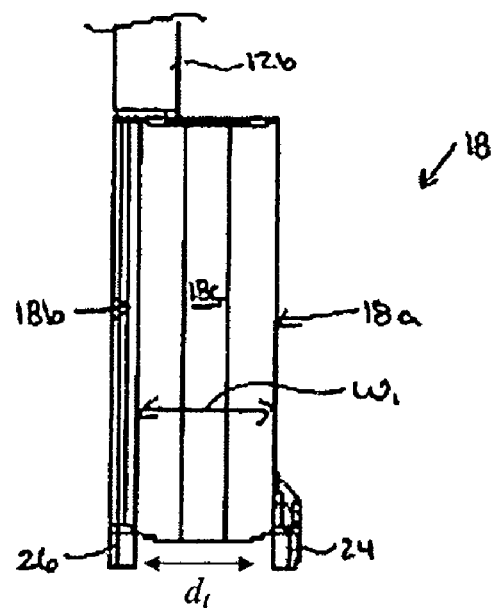
FIG. 2A is an enlarged side view of the guide member on the guide device shown in FIG. 1.
Figure 2B:
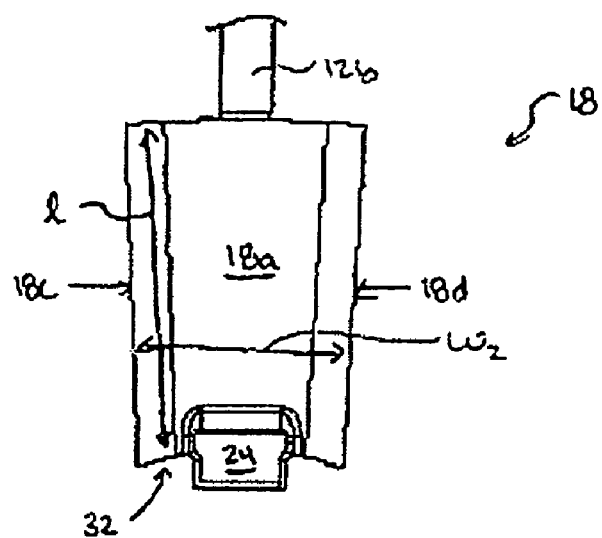
FIG. 2B is an enlarged front view of the guide member on the guide device shown in FIG. 1.

The guide member 18, which is shown in more detail in FIGS. 2A and 2B, can also have a variety of configurations, shapes, and sizes, but in an exemplary embodiment the guide member 18 preferably has a substantially rectangular, elongate shape. For reference purposes, each side of the guide member 18 will be referred to in accordance with its location when the guide member 18 is in use. Thus, the guide member 18 includes opposed superior and inferior sides 18a, 18b, and opposed first and second transverse sides 18c, 18d that extend between the opposed superior and inferior sides 18a, 18b. The transverse sides 18c, 18d preferably have a width $w_1$ that is less than a width $w_2$ of the superior and inferior sides 18a, 18b. The guide member 18 should, however, have a shape and size that results in the alignment of the lumens 20, 22 with corresponding bores formed in a spinal fixation element that is coupled to the device 10, as will be discussed below.

The guide member 18 also includes at least one pathway formed therein for receiving a tool, such as an awl, a drill bit, a fastener, or a driver device. While the at least one pathway can have a variety of configurations, FIGS. 1-2B illustrate first and second lumens 20, 22 formed in and extending through the guide member 18. The lumens 20, 22 are spaced apart from one another such that each lumen 20, 22 is positioned adjacent to a transverse side 18c, 18d of the guide member 18. The position or angle of the lumens 20, 22 with respect to one another can vary depending on the intended use, however the lumens 20, 22 should be adapted to align with corresponding thru bores formed in a spinal fixation element to provide a fixed entry angle for a device being inserted therethrough.

In use, the guide member 18 is adapted to interact with a spinal fixation element such that the lumens 20, 22, in the guide member 18 are aligned with corresponding bores formed in the spinal fixation element. Accordingly, in order to facilitate alignment of the guide member 18 with the spinal fixation element, a distal end surface 32 of the guide member 18 can be adapted to rest against a spinal fixation element. In an exemplary embodiment, the distal end surface 32 of the guide member 18 has a shape that is adapted to match the contour (in the transverse direction) of a spinal fixation element, such as a spinal fixation plate. As shown in FIG. 2B, for example, the distal end surface 32 of the guide member 18 can have a substantially concave shape that is adapted to rest against a spinal fixation plate having a convex surface.

Alignment between the guide member 18 and a spinal fixation element can also be achieved using one or more alignment elements formed on the guide member 18. Each alignment element can have a variety of configurations, and they can be adapted to interact with various features on a spinal fixation element. Moreover, the alignment element(s) can be configured to non-rigidly or rigidly couple to the spinal fixation element, and/or the alignment element(s) can interact with the spinal fixation element to either prevent rotation or to allow some rotation of the guide member 18 with respect to the spinal fixation element.

As shown in FIGS. 1-2B, guide member 18 includes opposed first and second alignment tabs 24, 26 extending distally therefrom, preferably such that the tabs 24, 26 are substantially parallel to one another. The tabs 24, 26 are effective to interact with edges formed on a spinal fixation element, such as a spinal fixation plate, to align the lumens 20, 22 in the guide member 18 with corresponding bores in the spinal fixation element. The shape, size, and position of each tab 24, 26 can vary, and they can be adapted to match the contour of particular portions of a spinal fixation element. In the illustrated embodiment, the tabs 24, 26 have a substantially rectangular shape and they are positioned on and they extend distally from the opposed superior and inferior surfaces 18a, 18b of the guide member 18 at a location that is substantially between the lumens 20, 22. As a result, one tab 24, 26 can be positioned against a superior or inferior edge of a spinal fixation element, and the other tab 24, 26 can be positioned on an edge of a graft window formed in the spinal fixation element, as will be discussed in more detail below. The location of the tabs on the superior and inferior surfaces 18a, 18b of the guide member 18 is particularly advantageous in that it prevents the tabs from impinging on any adjacent soft tissues that may be located at the lateral edges of the spinal fixation element when the guide member 18 is coupled to a spinal fixation element.

While the tabs 24, 26 preferably do not extend into any cut-out portions formed in the spinal fixation element, or otherwise include an engagement feature for engaging the spinal fixation element, the tabs 24, 26 can provide a clearance fit therebetween to minimize rotation of the guide member 18 with respect to the spinal fixation element when the tabs 24, 26 are aligned therewith. More preferably, the tabs 24, 26 can be adapted to provide a sliding interference fit with the spinal fixation element such that the tabs 24, 26 are effective to retain the spinal fixation element therebetween. This can be achieved by providing a distance $d_t$ (FIG. 2A) between the tabs 24, 26 that is less than a distance between the opposed edges formed on the spinal fixation plate that the tabs 24, 26 are configured to rest against, as will be discussed in more detail below. In use, some force may be required to position the tabs 24, 26 adjacent to opposed edges of the spinal fixation element, and the tabs 24, 26 may flex to fit around the spinal fixation element. However, once mated to the spinal fixation element, the guide device 10 can be used to manipulate the spinal fixation element. Subsequently, some force may likewise be required to remove the guide device 10 from the spinal fixation element. This is advantageous in that the tabs 24, 26 allow the guide member 18 to be quickly and easily positioned against, and subsequently removed from, the spinal fixation element.

In an alternative embodiment, the tabs 24, 26 can be configured to engage and/or fixedly interact with the spinal fixation element. By way of non-limiting example, the tabs can be formed from a compliant material that allows the tabs 24, 26 to flex to engage the spinal fixation element. In other embodiments, the tabs 24, 26 can be adapted to extend into corresponding slots formed in the spinal fixation element, and/or they can provide a snap-fit engagement with the spinal fixation element. For example, each tab 24, 26 can include a ridge formed thereon that is adapted to fit within a corresponding groove formed in an edge of the spinal fixation element or formed within a slot in the spinal fixation element. In this configuration, the tabs 24, 26 should be slightly flexible to allow the tabs to engage and disengage the spinal fixation element. Additional techniques for aligning the guide member 18 with a spinal fixation element will be discussed in more detail below.

Figure 3:
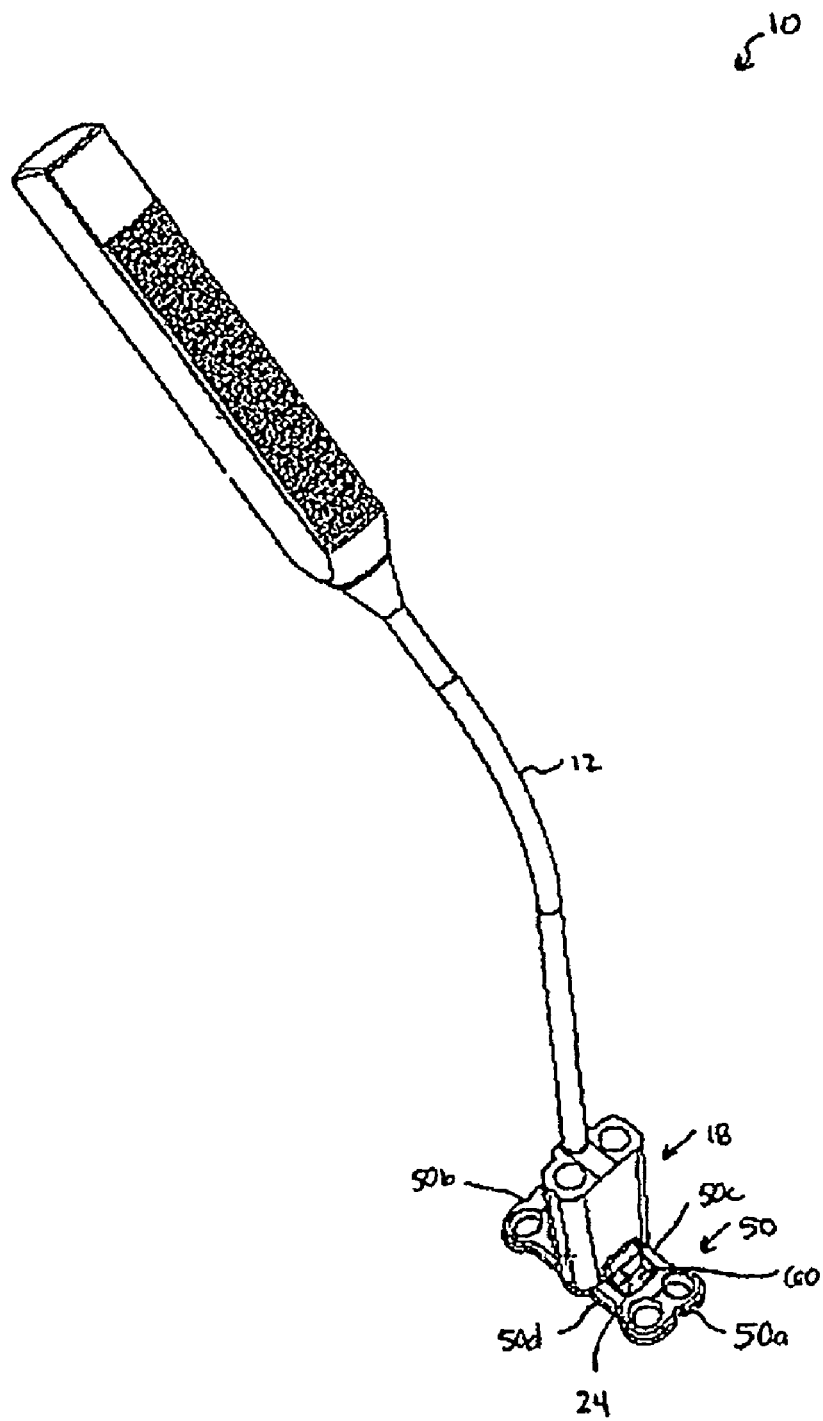
FIG. 3 is a perspective view of the guide device of FIG. 1 coupled to a pair of screw bores in a spinal fixation plate.
Figure 4:
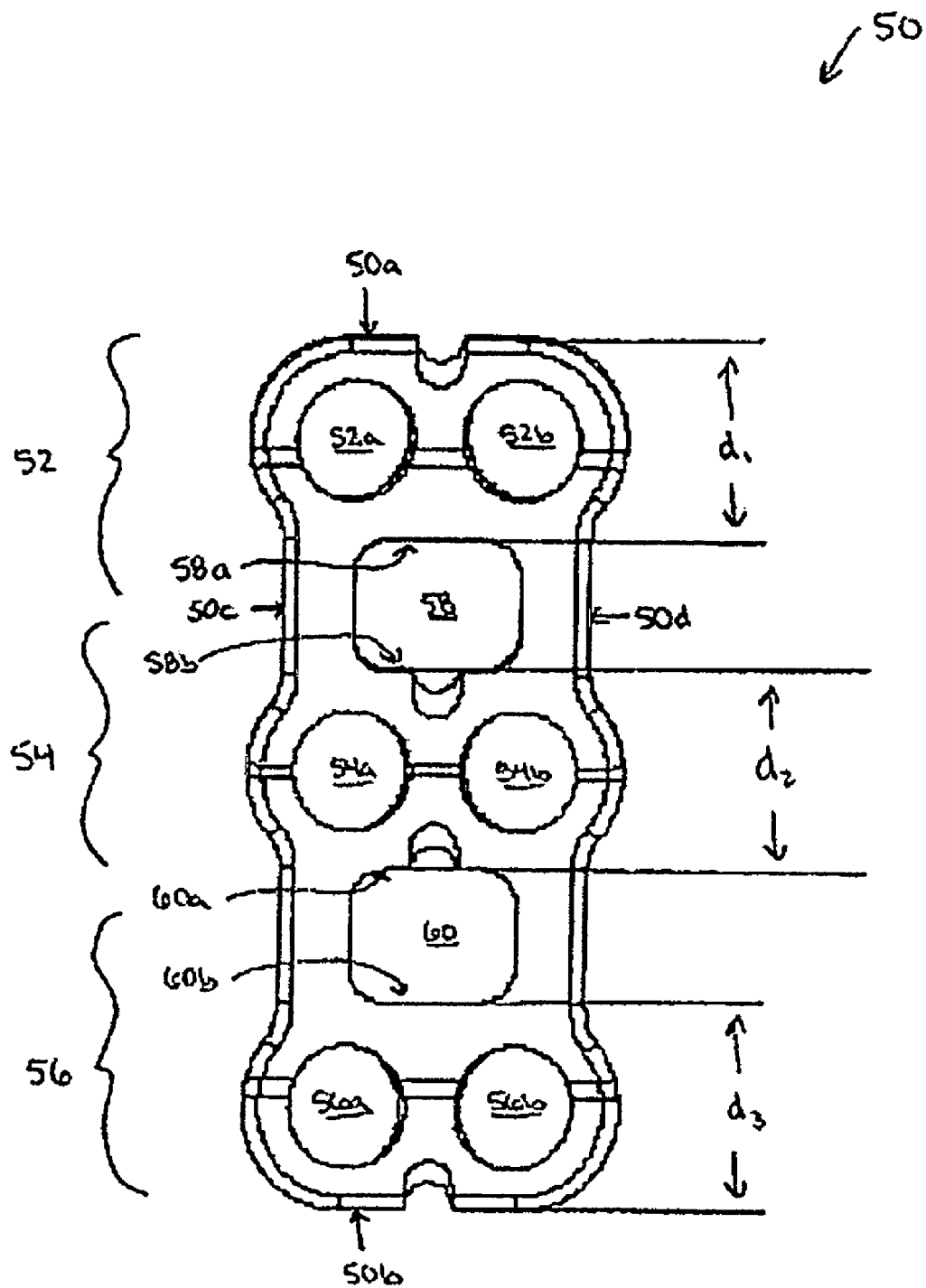
FIG. 4 is an enlarged perspective view of the spinal fixation plate of FIG. 3.

FIG. 3 illustrates device 10 mated to an exemplary embodiment of a spinal fixation element, i.e., spinal fixation plate 50, which is disclosed in more detail in U.S. patent application Ser. No. 10/664,238, filed Sep. 17, 2003 and entitled "Bone Fixation Plates." In general, the spinal fixation plate 50, which is shown separately in FIG. 4, includes four outer edges: a superior edge 50a, an inferior edge 50b, and first and second opposed lateral sides 50c, 50d. As shown in FIG. 4, a first pair of screw bores 52a, 52b is formed in a superior portion 52 of the spinal fixation plate 50, a second pair of screw bores 54a, 54b is formed a mid-portion 54 of the spinal fixation plate 50, and a third pair of screw bores 56a, 56b is formed an inferior portion 56 of the spinal fixation plate 50. The spinal fixation plate 50 also includes a first graft window 58 formed therein between the first and second pair of screw bores 52a, 52b, 54a, 54b, and a second graft window 60 formed therein between the second and third pair of screw bores 54a, 54b, 56a, 56b. The graft windows 58, 60 are configured such that the distance $d_1$ between the superior edge 50a of the spinal fixation plate 50 and a superior edge 58a of the first graft window 58 is equal to the distance $d_2$ between an inferior edge 58b of the first graft window 58 and a superior edge 60a of the second graft window 60, which is equal to the distance $d_3$ between an inferior edge 60b of the second graft window 60 and the inferior edge 50b of the spinal fixation plate 50. As noted above, each distance $d_1$, $d_2$, $d_3$ between the edges of the plate 50 is preferably greater than the distance $d_t$ (FIG. 2A) between the tabs 24, 26 such that the tabs 24, 26 provide a sliding interference fit with the plate 50.

In use, the opposed alignment tabs 24, 26 on the guide member 18 can be aligned with any one of the three pairs of screw bores 52a, 52b, 54a, 54b, 56a, 56b formed in the spinal fixation plate 50. By way of non-limiting example, FIG. 3 illustrates the guide member 18 aligned with the second pair of screw bores 54a, 54b formed in the mid-portion 54 of the spinal fixation plate 50. As shown, tab 24 is positioned adjacent to superior edge 60a of the second graft window 60, and tab 26 (not shown) is positioned adjacent to the inferior edge 58b of the first graft window 58.

FIGS. 5A-5D illustrate another embodiment of a guide device 510 in accordance with the present invention. The guide device 510 is similar to guide device 10 in that it includes an elongate shaft 512 having a proximal portion 512a, and a distal portion 512b that is coupled to a guide member 518. The guide member 518, however, does not include two separate lumens extending therethrough, but rather it includes first and second pathways 520, 522 formed within a single lumen extending therethrough between proximal and distal ends 519a, 519b thereof. As shown, each pathway 520, 522 is defined by a substantially semi-cylindrical or C-shaped sidewall. As a result, each pathway 520, 522 is configured to receive and guide a tool toward a spinal fixation element, such as a spinal fixation plate, positioned in relation to the guide member 518. A person skilled in the art will appreciate that the pathways 520, 522 can be only partially in communication with one another, or they can be separated from one another, and they can have a variety of other shapes and sizes. In addition, the first and second pathways can be positioned at an angle with respect to one another. For example, a central axis of the first pathway can be non-parallel to a central axis of the second pathway, such that the central axis of the first pathway and the central axis of the second pathway converge relative to one another.

As is further illustrated in FIGS. 5A-5D, the guide member 518 can also optionally include one or more cut-out portions or windows formed therein to facilitate visual access to a spinal fixation element coupled to the guide device 510. The cut-out portions can be formed anywhere in the guide member 518, but in an exemplary embodiment a first cut-out portion 528 is formed in a superior sidewall 518a of the guide member 518 between the first and second pathways 520, 522, and a second, opposed cut-out portion 529 is formed in the inferior sidewall 518b of the guide member 518. The first cut-out portion 528 extends from the proximal end 519a of the guide member 518 to the distal end 519b of the guide member 518, such that the superior sidewall 518a of the guide member 518 is separated into two sides. The second cut-out portion 529 extends proximally from the distal end 519b of the guide member 518 through a substantial portion of the guide member 518. The second cut-out portion 529, however, terminates just distal to the proximal end 519a of the guide member 518a to allow the lateral sidewalls 519c, 519d that define the pathways 520, 522 to remain coupled to one another, and to allow the elongate member 512 to mate to the guide member 518 at a substantial mid-portion thereof.

As previously indicated, the cut-out portions 528, 529 are particularly advantageous in that they provide the surgeon with improved visual access to a spinal fixation element positioned in relation to the guide member 518, as well as to the tools and devices used in connection with the guide device 510. At least one of the cut-out portions 528, 529 can also avoid interference by the guide member 518 with a temporary fixation pin that may be disposed through the spinal fixation element to temporarily attach the fixation element to bone. Since temporary fixation pins are typically only placed on opposed ends of a fixation element, such as a spinal fixation plate, the cut-out portion 528, 529 that is positioned adjacent to an end of the fixation element can receive at least a portion of a temporary fixation pin therebetween. A person skilled in the art will appreciate that the shape, size, and location of each cut-out portion 528, 529 can vary, and that the guide member 518 can include a variety of other cut-out portions and/or windows formed therein.

Figure 5A:
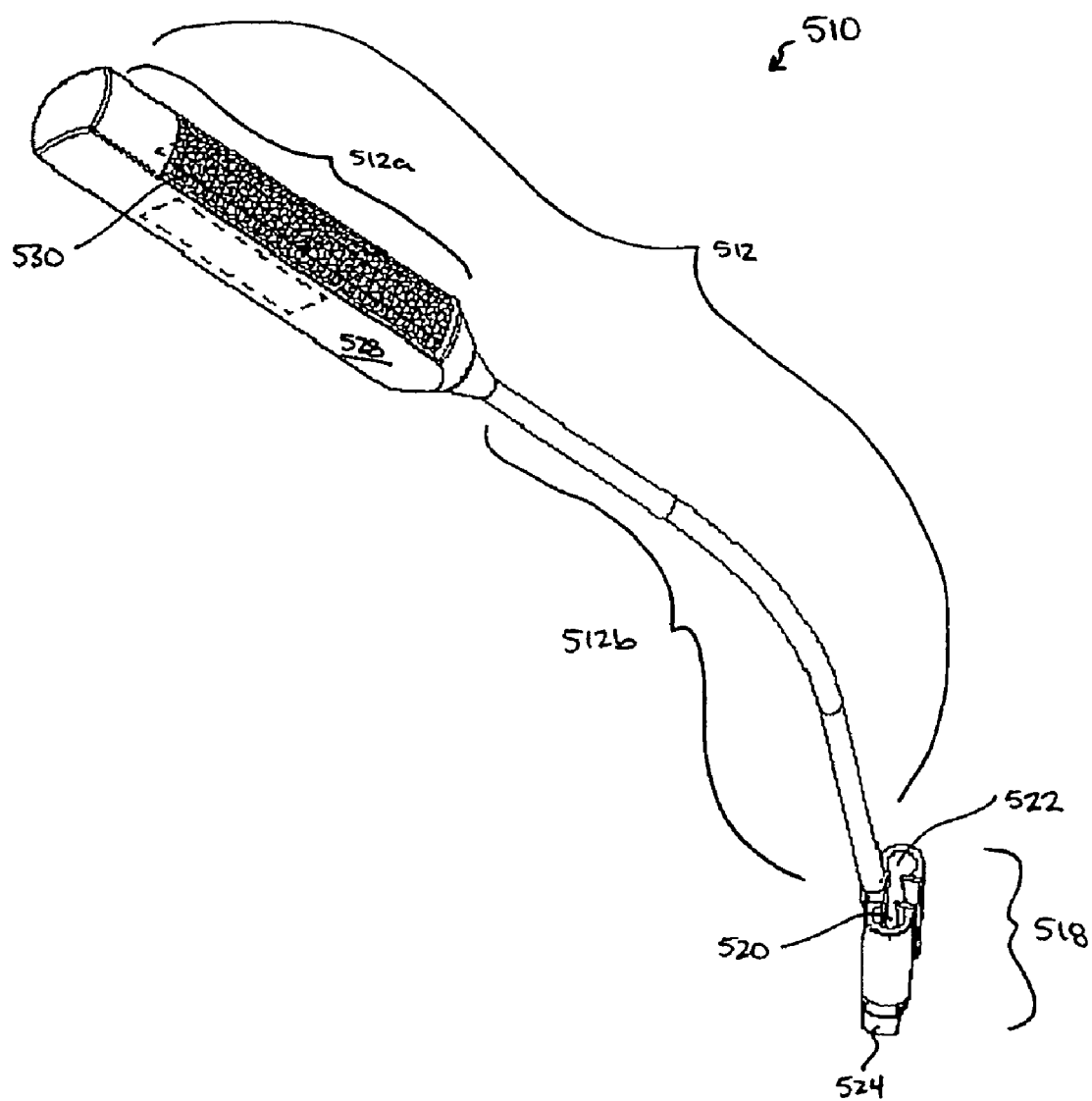
FIG. 5A is a perspective view of another embodiment of a guide device according to the present invention.
Figure 5B:
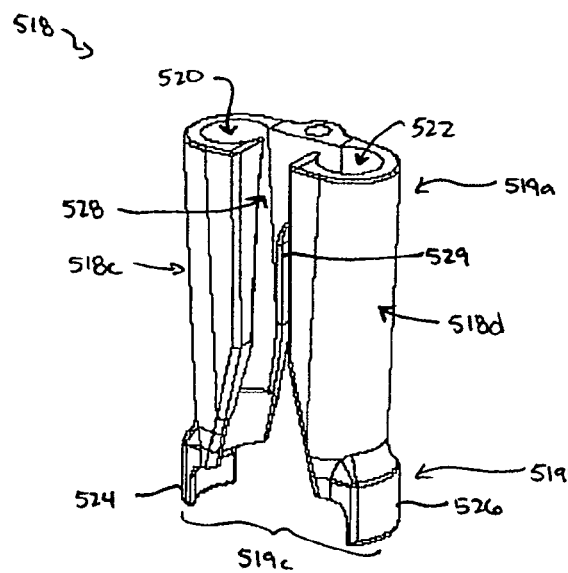
FIG. 5B is a side perspective view of the guide member of the guide device shown in FIG. 5A.
Figure 5C:
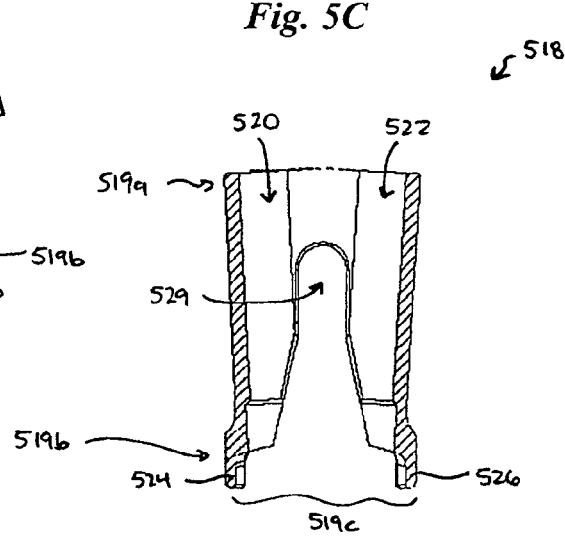
FIG. 5C is a cross-sectional view of the guide member shown in FIG. 5B.
Figure 5D:
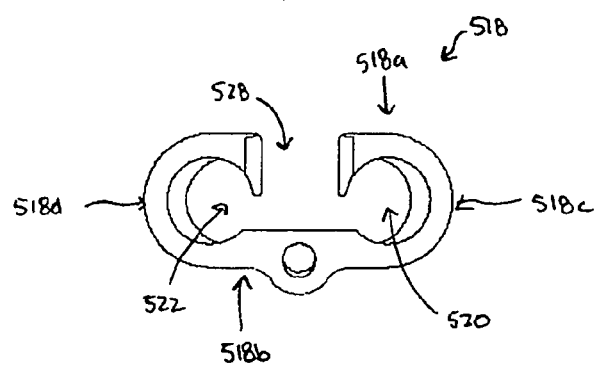
FIG. 5D is a top view of the guide member shown in FIG. 5B.

As previously discussed with respect to guide device 10, in use guide device 10' is preferably adapted to couple to or be juxtaposition on a spinal fixation element, and more preferably to a spinal fixation plate. Accordingly, the guide member 518 can include at least one mating element or alignment mechanism formed thereon for engaging or otherwise coupling to a spinal fixation element. As shown in FIGS. 5B-5C, the distal end 519b of the guide member 518 has a shape that is adapted to match the shape of a spinal fixation plate, and in particular the distal-most end portion 519c is substantially concave to seat a convex surface of the plate. The guide member 518 also includes distally-extending tabs 524, 526 formed on each sidewall 518c, 518d that are effective to seat a spinal fixation element therebetween. The tabs 524, 526 each preferably have a substantially concave inner surface such that they match the contour of a substantially convex outer surface formed around opposed thru bores formed in a spinal fixation element. This allows the tabs 524, 526 to rest against and/or engage opposed outer surfaces of the spinal fixation element. The tabs 524, 526 preferably do not, however, extend into any cut-out portions formed in the spinal fixation element, but they can be adapted to provide a sliding interference fit with outer edges of the spinal fixation element to engage the fixation element, as discussed above with respect to guide device 10. A person skilled in the art will appreciate that the guide member 518 can include any number of tabs formed on any sidewall thereof, and that the guide member 518 can include a variety of other mating elements, including those previously described with respect to guide device 10.

FIGS. 6A-6B illustrate a portion of another embodiment of a guide device 610 in accordance with the present invention. The device 610 is similar to guide devices 10 and 510, however the guide member 618 includes first and second barrels 619, 621 having lumens 620, 622 extending therethrough, respectively. The use of separate barrels 619, 621, rather than a housing, is particularly advantageous in that it provides improved visual access to a spinal fixation element coupled to the guide device 610. The barrels 619, 621 can also be advantageously configured to have an adjustable length, and/or an adjustable angle. The barrels 619, 621 can also optionally be removable to allow barrels having different lengths to be selected based on the intended use.

The guide member 618 show in FIGS. 6A-6B also includes tabs 624, 626 formed thereon to facilitate alignment of the guide member 618 with a spinal fixation element. The tabs 624, 626 are similar to tabs 524 and 526 on guide member 518 of guide device 510 in that they extend distally from opposed transverse sides 618c, 618d of the guide member 610 such that the lumens 620, 622 in the guide member 618 are positioned between the tabs 624, 626. As a result, the tabs 624, 626 will align with the opposed lateral side edges 50c', 50d' of a spinal fixation plate 50', as show in FIG. 6B. In this embodiment, each tab 624, 626 has a shape that conforms to a shape of the lateral edges 50c', 50d' of the spinal fixation plate 50' adjacent to screw bores 52a', 52b' formed in the spinal fixation plate 50'. In particular, the tabs 624, 626 have a concave shape, or at least a concave inner surface, that matches the convex shape of the spinal fixation plate 50' along the lateral edges 50c', 50d' of the spinal fixation plate 50 adjacent to the screw bores 52a', 52b' formed in the spinal fixation plate 50'.

Still referring to FIG. 6A, in addition to, or as an alternative to, the tabs 624, 626, the guide member 618 can include a mating element, such as a protrusion or pin member 40, that extends from a distal surface thereof. The pin member 40 can be formed at any location on the guide member 618, but it is preferably at a location that is substantially between the first and second lumens 620, 622. The pin member 40 is adapted to extend into a corresponding detent or bore 62 formed in the spinal fixation plate 50'. The pin member 40 can optionally extend at an angle to further facilitate grasping the spinal fixation plate 50'. In an exemplary embodiment, the pin member 40 is adapted to prevent rotation between the guide member 618 and the spinal fixation plate 50' to provide stability to the connection. By way of non-limiting example, mating elements with non-symmetrical shapes, such as a pin with a non-circular cross section (e.g., rectangular, oval, triangular, irregular), a multi-pronged mating element, or a tongue-and-groove combination, can prevent or reduce the tendency of the device 10' to pivot with respect to the spinal fixation plate 50'.

In another embodiment of the present invention, shown in FIG. 7, the guide device 710 can include a guide member 718 having a fixed tab 724 and an opposed deflecting tab 720 that is adapted to provide a friction fit between a spinal fixation element and the guide member 718. The deflecting tab 720 can include a fixed tab portion 726 positioned adjacent thereto to prevent the deflecting tab 720 from accidentally breaking. In this embodiment, the tabs 720, 724, 726 can be formed on opposed transverse sides of the guide member, or alternatively they can be formed on superior and inferior sides of the guide member.

Figure 8:
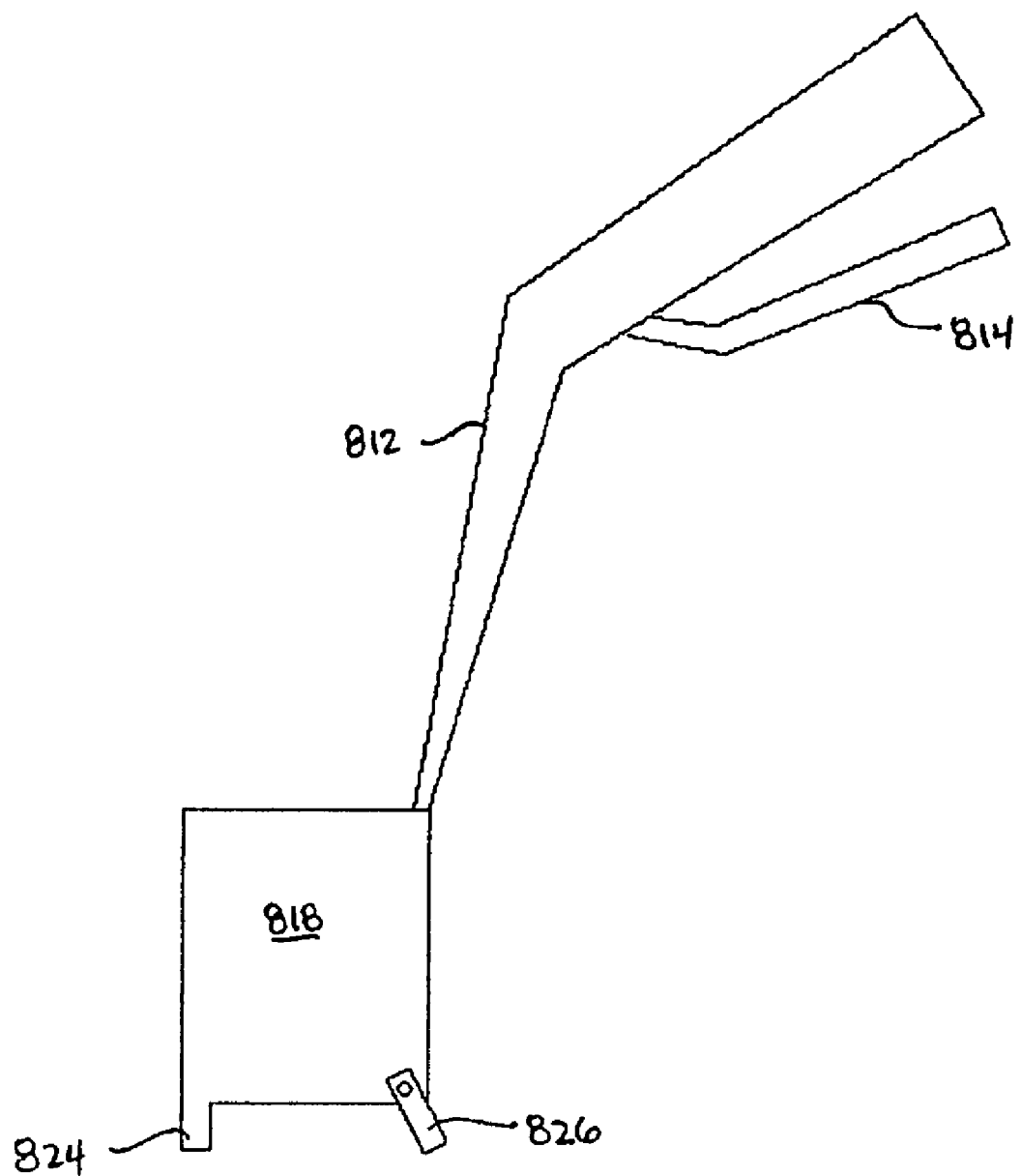
FIG. 8 is a side view illustration of a guide device having a pivotable alignment mechanism in accordance with another embodiment the present invention.

FIG. 8 illustrates yet another embodiment of a guide device 810 in which the guide member 818 includes a fixed tab 824 and a pivoting tab 826. The pivoting tab 826 can be coupled to a lever 814 that is formed on the handle of the shaft 812 for controlling the pivoting motion of the tab 826. A cable or similar element can extend between the lever 814 and the tab 826 for moving the tab 826 between open and closed positions. Again, like the embodiment illustrated in FIG. 7, the pivoting tab 826 and the fixed tab 824 can be formed on opposed transverse sides of the guide member 818, or alternatively they can be formed on superior and inferior sides of the guide member 818.

Figure 9A:
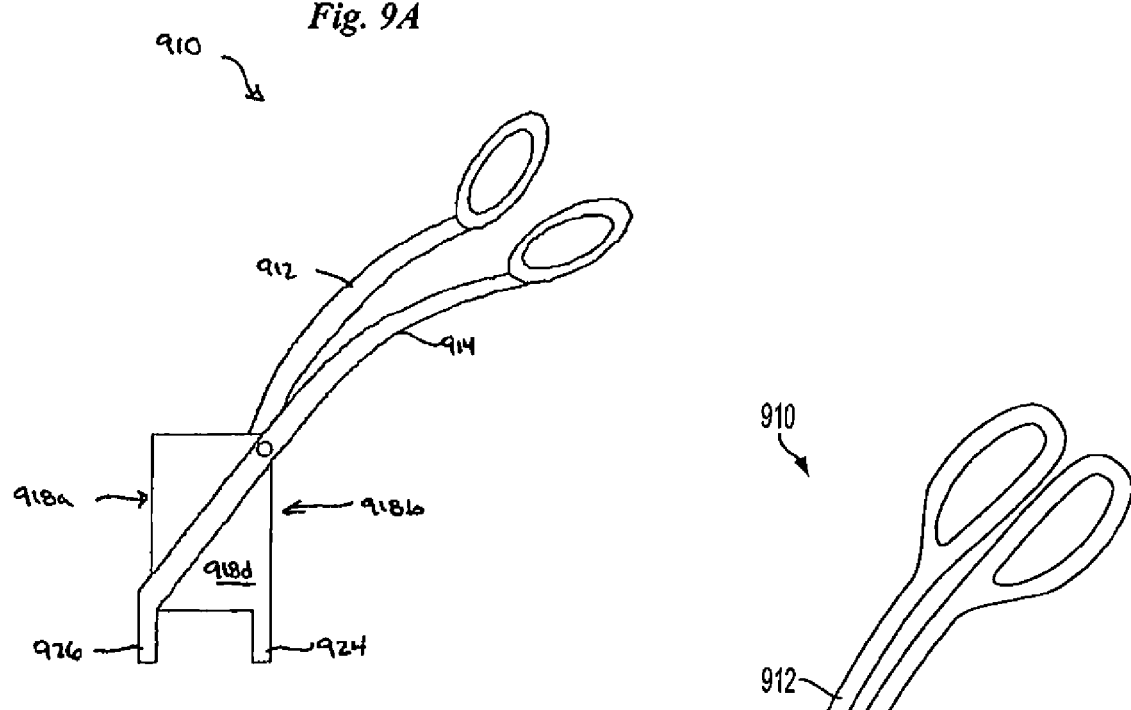
FIG. 9A is a side view illustration of yet another embodiment of a guide device in accordance with the present invention.
Figure 9B:
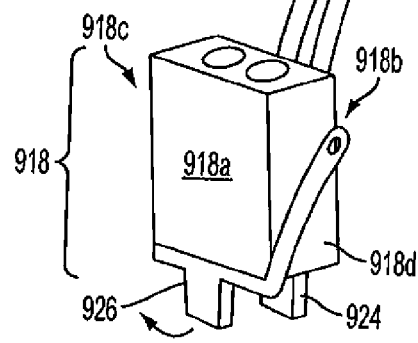
FIG. 9B is a perspective view illustration of the guide device of FIG. 9A.

FIGS. 9A and 9B illustrate a similar embodiment of a guide member 918 having a pivoting alignment mechanism 926. In this embodiment, the shaft is in the form of a first handle member 912, which is preferably fixed with respect to the guide member 918, and a second handle member 914 that is pivotally coupled to the guide member 918. An alignment tab 926 is formed on the distal portion of the second handle member 914, such that movement of the second handle member 914 is effective to move the alignment tab 926 between open and closed positions. The tab 926, in combination with an opposed fixed tab 924, is effective to engage a spinal fixation element therebetween when the alignment tab 926 is in the closed position. While FIG. 9B illustrates tabs 924, 926 formed on superior and inferior sides 918a, 918b of the guide member 918, the tabs 924, 926 can optionally be formed on opposed transverse sides 918c, 918d of the guide member for engaging lateral edges of a spinal fixation element. A person skilled in the art will appreciate that a variety of other techniques can be employed for providing at least one pivotable alignment mechanism, and in general for aligning the guide member with a spinal fixation element.

Figure 10A:
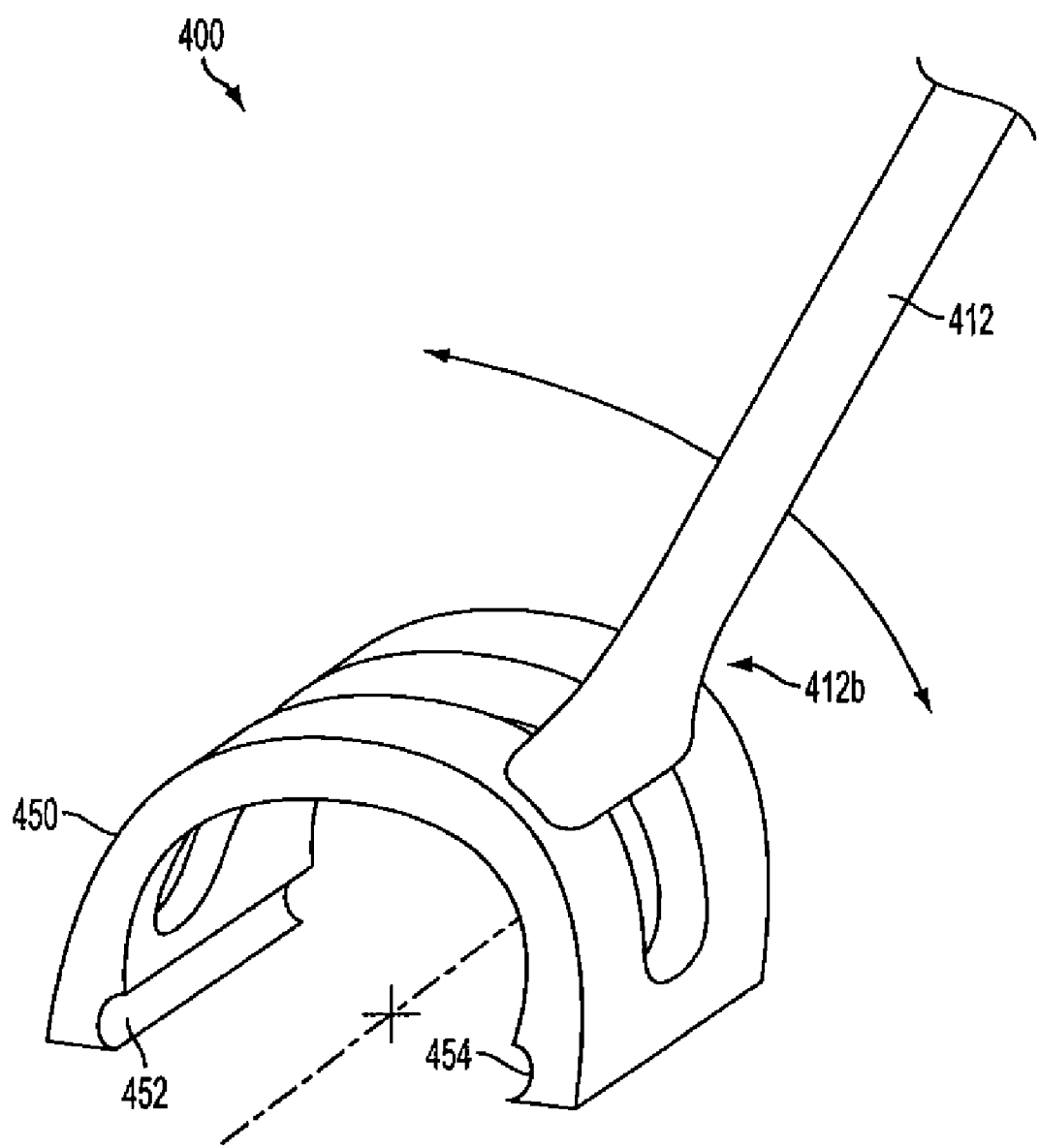
FIG. 10A is an enlarged perspective side view of a portion of a guide device having support member coupled to an elongate shaft in accordance with another embodiment of the present invention.
Figure 10B:
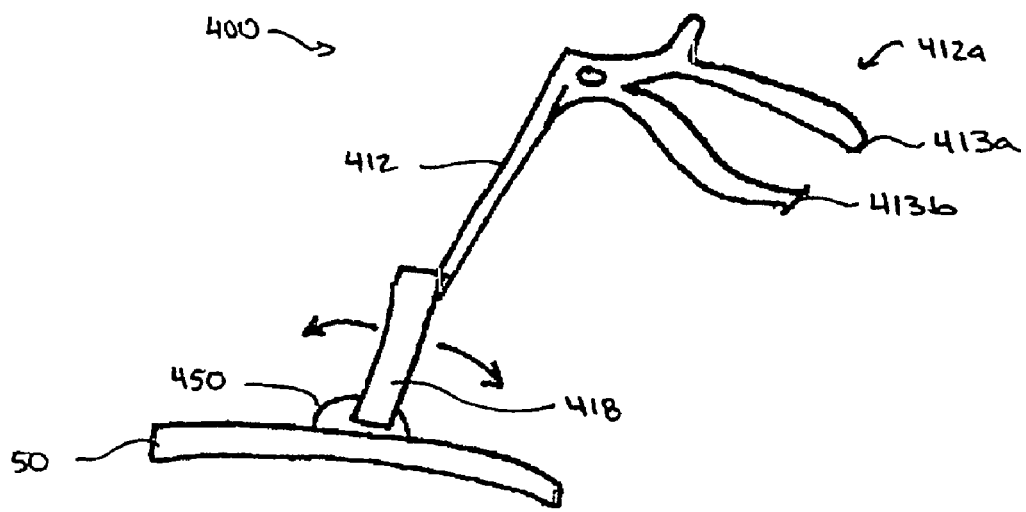
FIG. 10B is a perspective side view illustration of the guide device of FIG. 10A coupled to a spinal fixation plate.

The present invention also provides a guide device that includes a variable angle guide member, as shown in FIGS. 10A-10B. The guide device 400 is similar to guide device 10 described with respect to FIGS. 1-2B. However, the guide member 418 does not include alignment elements that are formed thereon and extending distally therefrom. While the alignment elements are positioned distal of the guide member 418, they are formed on a support member 450 that allows the angle of the guide member 418 to be adjusted.

Figure 10C:
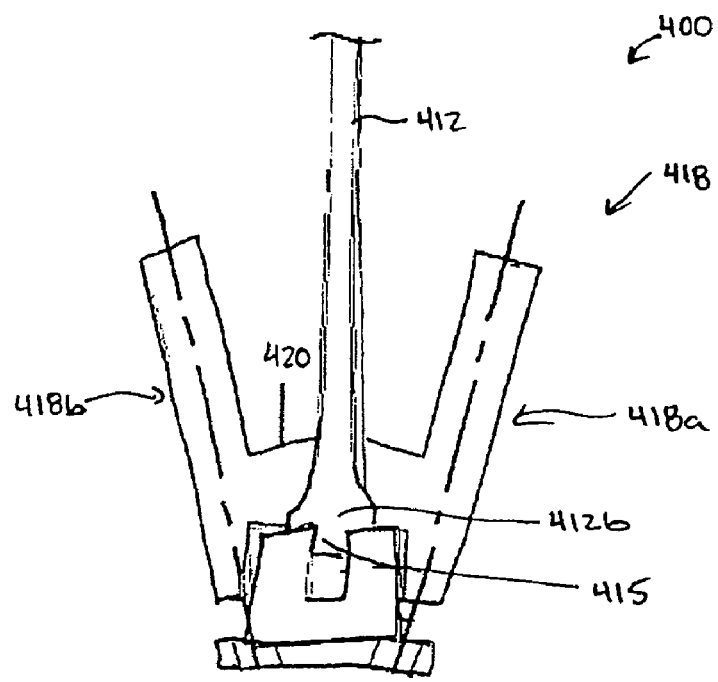
FIG. 10C is a perspective front view of a portion of the guide device and spinal fixation plate shown in FIG. 10B.

More particularly, as shown in FIGS. 10A-10C, the guide device 400 includes an elongate shaft 412 having a proximal, handle end 412a and a distal end 412b. The distal end 412b of the shaft 412 is slidably coupled to a support member 450 which is adapted to couple to a spinal fixation element, e.g., spinal fixation plate 50. A variety of techniques can be used to mate the distal end 412b of the shaft 412 to the support member 450, but it should be adjustable between several fixation positions. In an exemplary embodiment, as shown, the proximal, handle end 412a of the shaft includes first and second handles 413a, 413b that are effective to control movement of the shaft 412 with respect to the support member 450. One or both handles 413a, 413b can be movable, but preferably handle 413a is fixed, and handle 413b is a trigger that is pivotable such that movement of trigger 413b is effective to engage and disengage the support member 450. An engagement mechanism, such as a brake 415, can be coupled to the distal end 412b of the shaft for engaging the support member 450. In use, actuation of the trigger 413b is preferably effective to release the brake 415 to allow the shaft 412 to be slidably movable with respect to the support member 450. When the shaft 412 is in the desired position, the trigger 413b can then be released to cause the brake 415 to re-engage the support member 450. The handles 413a, 413b can also include a ratchet mechanism (not shown) or other engagement mechanism for temporarily maintaining the position of the first and second handles 413a, 413b with respect to one another. A person skilled in the art will appreciate that a variety of other techniques can be used to effect and/or control movement of the shaft 412 and/or the guide member 418 with respect to the support member 450.

The distal end 412b, in addition to being coupled to a support member 450, is coupled to a guide member 418. As shown in FIG. 10C, the guide member 418 includes first and second barrels 418a, 418b having lumens extending therethrough for receiving a tool. Each barrel 418a, 418b is mated to one another and to the distal end 412b of the shaft 412 by a connection member 420. The connection member 420 allows the barrel 412a, 412b to be positioned on opposed sides of the support member 450, and to extend distal of the support member 450 such that the barrels 418a, 418b can be positioned adjacent to a spinal fixation element that is coupled to the support member 450.

An exemplary support member 450 is shown in more detail in FIG. 10A, and it can have a variety of configurations. The support member 450 is, however, preferably arch-shaped to allow the angle of the shaft 412, and thus the angle of the guide member 418, to be adjusted as desired. The support member 450 should also be adapted to engage opposed edges formed on a spinal fixation element, and in particular to engage a superior or inferior edge and/or an edge of a graft window. As shown in FIG. 10A, the support member 450 includes a substantially concave groove 452, 454 formed on an inner surface of each end of the support member 450. The opposed grooves 452, 454 are configured to fit around opposed edges of a spinal fixation element. A person skilled in the art will appreciate that a variety of other techniques, including those described herein, can be used to couple the support member 450 to a spinal fixation element. In an exemplary embodiment, however, the support member 450 should rigidly connect to or at least temporarily engage the spinal fixation element to prevent removal of the support member 450 during adjustment of the guide member 418.

The guide device of the present invention can also be provided as part of a spinal fixation kit that includes a spinal fixation element having at least one thru bore formed therein for receiving a fastening element that is effective to mate the spinal fixation element to at least one vertebrae. The spinal fixation element, e.g., a spinal fixation plate, can also include at least one graft window formed therein that is adjacent to at least one pair of opposed thru bores formed in the spinal fixation element. The kit can include additional devices, tools, and/or implants, such as fastening devices, bone preparation devices, etc.

The guide devices of the present invention can be used to implant a variety of spinal fixation elements, and once the spinal fixation element is properly positioned against the spine and the guide device is aligned with the spinal fixation element, implants, tools, and/or devices, such as, for example, a drill, awl, tap, or bone screw, can be passed through the each pathway in the guide member to prepare the vertebrae and/or to couple a spinal implant to the vertebrae.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A guide device for use with a spinal fixation element, the guide device comprising:
    an elongate shaft having a proximal end with a handle disposed thereon and a distal end;
    a guide member mated to the distal end of the elongate shaft and having opposed superior and inferior sides, opposed first and second transverse sides extending between the superior and inferior sides, and proximal and distal ends, the guide member having first and second pathways formed within a single lumen and extending therethrough between the proximal and distal ends of the guide member, the first and second pathways having central axes that extend in a plane that is parallel to the superior and inferior sides of the guide member, the distal end of the elongate shaft being offset from the first and second pathways;
    at least one alignment tab extending distally beyond the distal end of the guide member, the at least one alignment tab being configured to interact with a spinal fixation element to position the guide member with respect to the spinal fixation element such that the first and second pathways in the guide member are aligned with a pair of corresponding thru bores formed in the spinal fixation element; and
    a cut-out portion formed in at least one of the superior and inferior sides of the guide member, the cut-out portion extending from the distal end of the guide member toward a proximal end of the guide member.

2. The guide device of claim 1, wherein the cut-out portion is at least partially in communication with the first and second pathways to provide visual access to at least a portion of the first and second pathways.

3. The guide device of claim 1, wherein the at least one alignment tab comprises opposed first and second alignment tabs extending from the first and second transverse sides.

4. The guide device of claim 1, wherein the at least one alignment tab has a substantially concave inner surface configured to rest against a substantially convex outer surface of a spinal fixation element.

5. The guide device of claim 1, further comprising at least one protrusion extending distally from the guide member and configured to be disposed within a corresponding bore formed in the spinal fixation element.

6. The guide device of claim 1, wherein the guide member has a substantially rectangular, elongate shape.

7. The guide device of claim 1, wherein the first and second transverse sides having a width extending therebetween that is less than a width extending between the superior and inferior sides.

8. The guide device of claim 1, wherein the first and second pathways are positioned at an angle with respect to one another.

9. The guide device of claim 1, wherein the cut-out portion comprises a first cut-out portion formed in the superior sidewall, and the guide member further comprises a second cut-out portion formed in the inferior sidewall.

10. The guide device of claim 1, wherein at least a portion of each pathway is defined by a substantially elongate, semi-cylindrical sidewall of the housing.

11. A guide device for use with a spinal fixation element, the guide device comprising:
    a non-cannulated elongate shaft having proximal and distal ends;
    a guide member coupled to the distal end of the elongate shaft and having a first substantially C-shaped lateral sidewall defining a first pathway extending through the guide member for guiding implants, tools, and devices therethrough, and a second substantially C-shaped lateral sidewall defining a second pathway extending through the guide member for guiding implants, tools, and devices therethrough, the first and second substantially C-shaped lateral sidewalls being coupled to one another along at least a portion of an inferior side of the guide member, and being spaced apart from one another along a superior side of the guide member; and
    at least one alignment element extending distally from a distal end of one of the first and second substantially C-shaped lateral sidewalls and configured to abut against an edge of a spinal fixation element to align the first and second pathways of the guide member with first and second thru-bores formed in the spinal fixation element.

12. The guide device of claim 11, wherein the superior side of the guide member includes a cut-out formed therein that separates the first and second substantially C-shaped lateral sidewalls.

13. The guide device of claim 11, wherein the inferior side of the guide member includes a cut-out formed therein and extending from a distal end and terminating distal to a proximal end of the guide member.

14. The guide device of claim 11, wherein the alignment element comprises a first alignment tab extending distally from a distal end of the first substantially C-shaped lateral sidewall, and a second alignment tab extending distally from a distal end of the second substantially C-shaped lateral sidewall.

15. A guide device for use with a spinal fixation element, comprising:
    a guide member defining first and second lumens extending therethrough between proximal and distal ends thereof, the first and second lumens having central axes that extend in a plane that is parallel to superior and inferior sides of the guide member, the central axis of the first lumen and the central axis of the second lumen converging relative to one another;
    first and second alignment tabs extending from a distal end of opposed lateral sides of the guide member such that first and second alignment tabs intersect the plane containing the axes of the first and second lumens;
    a first cut-out formed in the superior side of the guide member that extends proximally from the distal end of the guide member and that is in communication with the first and second lumens such that the cut-out provides visual access to implants, tools, and devices disposed through the first and second lumens; and a second cut-out formed in the inferior side of the guide member and extending proximally from the distal end of the guide member.

16. The guide device of claim 15, wherein the first and second alignment tabs each have a substantially concave inner surface configured to rest against a substantially convex outer surface of a spinal fixation element.

17. The guide device of claim 15, further comprising at least one protrusion extending distally from the distal end of the guide member and configured to be disposed within a corresponding bore formed in the spinal fixation element.

18. The guide device of claim 15, wherein the first and second lumens are positioned at a fixed angle with respect to one another.

* * * * *